United States Patent [19]

Tokiwa et al.

[11] Patent Number: 5,859,217
[45] Date of Patent: Jan. 12, 1999

[54] PROCESS FOR PRODUCING POLYMERIZATION SUGAR ESTERS

[75] Inventors: Yutaka Tokiwa, Tsuchiura; Shigeo Shibatani, Kyoto, both of Japan

[73] Assignees: Director-General of Agency of Industrial Science and Technology; Research Institute of Innovative Technology for the Earth; Toyo Boseki Kabushiki Kaisha, all of, Japan

[21] Appl. No.: 674,810

[22] Filed: Jul. 3, 1996

[30] Foreign Application Priority Data

Nov. 27, 1995 [JP] Japan ................................. 7-331051

[51] Int. Cl.[6] ...................................................... C07H 1/00
[52] U.S. Cl. ........................... 536/1.11; 536/32; 536/124; 435/72
[58] Field of Search ............................. 536/1.11, 32, 111, 536/115, 119, 124; 435/101, 72

[56] References Cited

U.S. PATENT DOCUMENTS 5,474,915   12/1995   Doudick et al. ........................... 435/72
5,488,102    1/1996   Vetten ....................................... 536/32

Primary Examiner—Ralph Gitomer
Attorney, Agent, or Firm—Lorusso & Loud

[57] ABSTRACT

Disclosed are a polymerizable sugar ester of the formula shown below and a process for the production thereof:

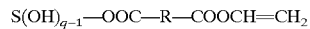

wherein $S(OH)_{q-1}$, represents a sugar residue obtained by removing one hydroxyl group from a sugar compound composed of a sugar skeleton S and q number of hydroxyl groups bonded thereto, and R represents an alkylene group. The polymerizable sugar ester is produced by reacting a sugar compound represented by the following general formula:

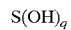

wherein S represents the sugar skeleton and q is the number of the hydroxyl groups bonded thereto, with a divinyl ester of an aliphatic dicarboxylic acid represented by the following general formula:

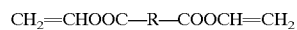

in the presence of a hydrolytic enzyme. The polymerizable sugar ester gives a sugar-based polymer by polymerization.

3 Claims, No Drawings

PROCESS FOR PRODUCING POLYMERIZATION SUGAR ESTERS

BACKGROUND OF THE INVENTION

The present invention relates to polymerizable sugar esters and a process for the production thereof.

One known vinyl group-containing sugar compound is sucrose acrylate (Macromolecules, vol. 24, p3462–2463 (1991); and U.S. Pat. No. 5,474,915). The sucrose acrylate is produced by reacting a mixture of sucrose and vinyl acrylate in an organic solvent in the presence of an enzyme.

The sucrose acrylate gives a sugar-based polymer by addition polymerization thereof through the double bond thereof. The sugar-based polymer is utilizable as a biodegradable plastic.

The sucrose acrylate is represented by the formula:

$$S-OCOCR=CH_2$$

wherein S represents a sucrose residue and R represents a hydrogen atom or a hydrocarbyl group. Since the spacer portion (—OCO—) between the vinyl group and the sugar molecule of the sucrose acrylate is short, it is difficult for the polymer obtained by the polymerization thereof to sufficiently function as a sugar.

SUMMARY OF THE INVENTION

It is the prime object of the present invention to provide polymerizable sugar esters having a structure in which a vinyl group is bonded to a sugar molecule through a carbon chain having at least three carbon atoms.

Another object of the present invention is to provide a process for the production of the polymerizable sugar esters.

In accordance with one aspect of the present invention there is provided polymerizable sugar esters represented by the following general formula (1):

$$S(OH)_{q-1}-OOC-R-COOCH=CH_2 \qquad (1)$$

wherein $S(OH)_{q-1}$ represents a sugar residue obtained by removing one hydroxyl group from a sugar compound composed of a sugar skeleton S and q number of hydroxyl groups bonded thereto, and R represents an alkylene group.

In another aspect, the present invention provides a process for the production of polymerizable sugar esters represented by the above general formula (1), wherein sugar compounds represented by the following general formula (2):

$$S(OH)_q \qquad (2)$$

wherein S represents the sugar skeleton and q is the number of the hydroxyl groups bonded thereto, are reacted with a divinyl ester of an aliphatic dicarboxylic acid represented by the following general formula (3):

$$CH_2=CHOOC-R-COOCH=CH_2 \qquad (3)$$

wherein R represents an alkylene group, in the presence of a hydrolytic enzyme.

DETAILED DESCRIPTION OF THE INVENTION

The present invention provides polymerizable sugar esters represented by the following general formula (1):

$$S(OH)_{q-1}-OOC-R-COOCH=CH_2 \qquad (1)$$

wherein $S(OH)_{q-1}$ represents a sugar residue obtained by removing one hydroxyl group from a sugar compound composed of a sugar skeleton S and q number of hydroxyl groups bonded thereto, and R represents an alkylene group.

The present invention also provides a process for the production of polymerizable sugar esters represented by the following general formula (1):

$$S(OH)_{q-1}-OOC-R-COOCH=CH_2 \qquad (1)$$

wherein $S(OH)_{q-1}$ represents a sugar residue obtained by removing one hydroxyl group from a sugar compound composed of a sugar skeleton S and q number of hydroxyl groups bonded thereto, and R represents an alkylene group, characterized in that a sugar compound represented by the following general formula (2):

$$S(OH)_q \qquad (2)$$

wherein S represents the sugar skeleton and q is the number of the hydroxyl groups bonded thereto, is reacted with a divinyl ester of an aliphatic dicarboxylic acid represented by the following general formula (3):

$$CH_2=CHOOC-R-COOCH=CH_2 \qquad (3)$$

wherein R represents an alkylene group, in the presence of a hydrolytic enzyme.

The sugar compound used in the present invention includes natural and synthetic sugars such as monosaccharides, oligosaccharides, polysaccharides and hydrolyzed products of polysaccharides. These sugar compounds may be represented by the following general formula (2):

$$S(OH)_q \qquad (2)$$

wherein S represents the sugar skeleton and q is the number of the hydroxyl groups bonded thereto.

Examples of monosaccharides include glucose, fructose, mannose and galactose. Examples of oligosaccharides include sucrose, maltose, cellobiose, lactose and raffinose. Examples of polysaccharides include starch, cellulose, chitin, chitosan, mannan, pullulan and cardran. Examples of the hydrolyzed products of polysaccharides include those obtained by hydrolyzing the above-mentioned polysaccharides using an enzyme or an acid. The sugar compound may be an ester of a higher fatty acid having 8–22 carbon atoms.

The divinyl esters of aliphatic dicarboxylic acids are represented by the following general formula (3):

$$CH_2=CHOOC-R-COOCH=CH_2 \qquad (3)$$

wherein R represents an alkylene group.

In the general formula (3), the alkylene group R is an alkylene group having at least one carbon atom and preferably an alkylene group having 2–8 carbon atoms. Illustrative of the divinyl esters of aliphatic dicarboxylic acid are those derived from aliphatic dicarboxylic acids such as malonic acid, succinic acid, glutaric acid, adipic acid, pimelic acid, suberic acid, azelaic acid, sebacic acid, nonanedicarboxylic acid and dodecanedicarboxylic acid.

The hydrolytic enzyme used in the present invention may be customarily used ones such as various kinds of proteases, e.g. protease derived from the strain of Streptomyces or the strain of Bacillus. It is preferred that the enzyme be used in the form of powder. Thus, it is advisable use to a liquid enzyme after the conversion thereof into a powder form by liophylization.

The polymerizable sugar ester according to the present invention is produced by reacting a sugar compound with a divinyl ester of an aliphatic dicarboxylic acid in a reaction solvent in the presence of a hydrolytic enzyme. The reaction may be represented by the following formula:

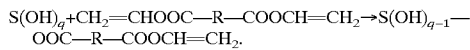
$$S(OH)_q + CH_2=CHOOC\text{—}R\text{—}COOCH=CH_2 \rightarrow S(OH)_{q-1}\text{—}OOC\text{—}R\text{—}COOCH=CH_2.$$

The above reaction is performed at a temperature of 30°–70° C., preferably 30°–50° C. Any reaction solvent may be arbitrarily used as long as it can dissolve the reaction raw materials and is liquid under the reaction conditions. Illustrative of suitable solvents are organic solvents such as dimethylformamide and dimethylsulfoxide. The concentration of the sugar compound in the reaction solvent is 1–20% by weight, preferably 10–20% by weight. The divinyl ester of an aliphatic dicarboxylic acid is used in an amount of 1–10 equivalents, preferably 1–5 equivalents per equivalent of the sugar compound. The hydrolytic enzyme is used in an amount of 0.1–20% by weight, preferably 0.1–1% by weight, based on the reaction solvent.

The hydroxyl group of the sugar compound with which the divinyl ester of an aliphatic dicarboxylic acid is reacted is the hydroxyl group bonded to the carbon atom at 6-position of the glucose or the hydroxyl group bonded to the carbon atom at 1-position of the fructose.

The sugar ester according to the present invention, which has vinyl groups in the molecules thereof, may be used as a polymerizable monomer. To produce a homopolymer or a copolymer using the sugar ester of the present invention as a polymerizable monomer, the sugar ester of the present invention is polymerized by itself or copolymerized with another polymerizable compound (such as a vinyl monomer or ketene acetal) by conventional polymerization methods such as a radical polymerization method. The thus obtained homopolymer shows high hydrophilicity and excellent biodegradability because of the function of the sugar contained therein. The hydrophilic and hydrophobic properties of the copolymer may be controlled by varying the proportions of the components thereof and excellent biodegradability is obtainable.

Since the spacer portion between the vinyl group and the sugar molecule in the sugar ester of the present invention is composed of —OCO—R—COO— and includes a carbon chain having 3 or more carbon atoms, the polymer obtained from the sugar ester can sufficiently exhibit the function inherent to the sugar. Further, there is obtained the advantage that the physical properties of the polymer obtained from the sugar ester of the present invention may be controlled by the length of the carbon chain R.

The present invention will be further described in detail by way of examples.

EXAMPLE 1

Into 50 ml of dimethylformamide (DMF) which had been sufficiently dried with a molecular sieve (3A) were dissolved 4.28 g of maltose $[C_{12}H_{11}(OH)_{11}]$ and 9.91 g of divinyl adipate. In the resulting solution were suspended 250 mg of alkaline protease (manufactured by Toyo Boseki Inc.) derived from the strain of Streptomyces. The enzyme-containing reaction mixture was then stirred at 35° C. at 130 rpm for 7 days. The reaction mixture was then measured for the sucrose concentration by high performance liquid chromatography using an amino-column (manufactured by TOSOH Inc., TSK gel Amide-80). Acetonitrile/water (75:25) was passed at a flow rate of 1.0 ml/minute. A differential refractometer was used as a detector. As a result, more than 80% of sucrose conversion was revealed. The DMF in the enzyme reaction mixture was then removed by a rotary evaporator and the residue was mixed with 50 ml of water and 50 ml of chloroform. The chloroform layer containing unreacted divinyl adipate was separated and the water was removed from the aqueous layer with a rotary evaporator. The residue was applied on a column (inside diameter: 1.5 cm, length: 30 cm) packed with silica gel (manufactured by Merck Inc., Kieselgel 60). The elution was then performed using a mixed solvent of ethyl acetate/methanol/water (17:2:1). The eluate was collected with a fraction collector for the separation of the products. Each fraction was analyzed by thin layer chromatography. Thus, each fraction was applied to a TLC plate (manufactured by Merck Inc., Kieselgel 60F) and eluted with a mixed solvent of ethyl acetate/methanol/water (17:2:1). The spots were developed with sulfuric acid to confirm the production of the sugar ester. The solvent of the sugar ester fraction was removed by a rotary evaporator and the sugar ester was analyzed by infrared. As a result, C=O and $CH_2$=CH stretching vibrations were found at 1740 and 1640 cm$^{-1}$, respectively, indicating that the product was a vinyl group-containing ester. The $^{13}$C-NMR analysis revealed a downfield shift of the carbon of maltose at 6'-position and an upfield shift of the carbon at 5'-position as well as the shifting of —CH$_2$— derived from divinyl adipate. Thus, it was confirmed that the sugar ester was 6'-O-vinyl adipate-maltose of the following formula:

$$[C_{12}H_{11}(OH)_{10}]\text{—}OOC(CH_2)_4COOCH=CH_2 \tag{5}$$

EXAMPLE 2

Into 50 ml of DMF which had been sufficiently dried with a molecular sieve (3A) were dissolved 4.28 g of sucrose $[C_{12}H_{11}(OH)_{11}]$ and 9.91 g of divinyl adipate. In the resulting solution were suspended 250 mg of alkaline protease (manufactured by Promega Inc.) derived from the strain of *Bacillus licheniformis*. Thereafter, the procedures of Example 1 was repeated in the same manner as described. As a result, more than 80% of maltose conversion were revealed. The sugar ester was analyzed by infrared and C=O and $CH_2$=CH stretching vibrations were found at 1740 and 1640 cm$^{-1}$, respectively, indicating that the product was a vinyl group-containing ester. The $^{13}$C-NMR analysis revealed a downfield shift of the carbon of sucrose at 1'-position and an upfield shift of the carbon at 2'-position as well as the shifting of —CH$_2$— derived from divinyl adipate. Thus, it was confirmed that the sugar ester was 1'-O-vinyl adipate-sucrose of the following formula:

$$[C_{12}H_{11}(OH)_{10}]\text{—}OOC\ (CH_2)_4COOCH=CH_2 \tag{6}$$

The sugar ester according to the present invention has a structure in which a vinyl group is bonded to a sugar molecule through a carbon chain and has a function as a sugar and is polymerizable because of the presence of the vinyl group.

The sugar ester according to the present invention may be utilized as a polymerizable monomer for obtaining a homopolymer or a copolymer with the utilization of the polymerizability of the vinyl group. The homopolymer or copolymer obtained by the polymerization of the sugar ester of the present invention has a structure in which a number of sugar molecules are bonded to the molecular chain thereof and, hence, is advantageously utilizable as a biodegradable plastic in the field of high molecular weight polymers and in the medical field.

What is claimed is:

1. A process for producing a polymerizable sugar ester represented by the following general formula (1):

$$S(OH)_{q-1}-OOC-R-COOCH=CH_2 \quad (1)$$

wherein $S(OH)_{q-1}$ represents a sugar residue obtained by removing one hydroxyl group from a sugar compound composed of a sugar skeleton S and q number of hydroxyl groups bonded thereto, and R represents a four carbon atoms alkylene group, said process comprising:

reacting a sugar compound represented by the following general formula (2):

$$S(OH)_q \quad (2)$$

wherein S represents the sugar skeleton and q is the number of the hydroxyl groups bonded thereto, with a divinyl ester of adipic acid acid represented by the following general formula (3):

$$CH_2=CHOOC-R-COOCH=CH_2 \quad (3)$$

wherein R represents the alkylene group, in the presence of a protease.

2. A process as claimed in claim 1, wherein said protease is derived from a strain of Streptomyces.

3. A process as claimed in claim 1, wherein said protease is derived from a strain of Bacillus.

* * * * *

UNITED STATES PATENT AND TRADEMARK OFFICE
CERTIFICATE OF CORRECTION

PATENT NO. : 5,859,217
DATED : January 12, 1999
INVENTOR(S) : TOKIWA et al

It is certified that error appears in the above-indentified patent and that said Letters Patent is hereby corrected as shown below:

Title page, item [54] and col. 1, line 2,
<u>IN THE TITLE</u>: "POLYMERIZATION" should read --POLYMERIZABLE--.

Signed and Sealed this

Thirtieth Day of November, 1999

Attest:

Q. TODD DICKINSON

*Attesting Officer*  *Acting Commissioner of Patents and Trademarks*